(12) United States Patent
Weber et al.

(10) Patent No.: US 6,489,518 B1
(45) Date of Patent: Dec. 3, 2002

(54) PROCESS FOR REDUCING THE SALT CONTENT OF FRACTIONS COMPRISING HIGH BOILERS OBTAINED IN THE PREPARATION OF PHENOL FROM CUMENE, BY EXTRACTION

(75) Inventors: Manfred Weber; Markus Weber, both of Haltern; Heinrich van Barneveld, Bottrop, all of (DE); Peter Bickert, Atlanta, GA (US); Wilfried Jordan, Dorsten (DE)

(73) Assignee: Phenolchemie GmbH & Co. KG, Gladbeck (DE)

( * ) Notice: Subject to any disclaimer, the term of this patent is extended or adjusted under 35 U.S.C. 154(b) by 0 days.

(21) Appl. No.: 09/709,353

(22) Filed: Nov. 13, 2000

(30) Foreign Application Priority Data

Nov. 11, 1999 (DE) ........................................ 199 54 141

(51) Int. Cl.$^7$ ............................................. C07C 37/68
(52) U.S. Cl. ...................... 568/749; 423/449.9; 568/754
(58) Field of Search ................................ 568/754, 749; 423/449.9

(56) References Cited

U.S. PATENT DOCUMENTS

| | | | |
|---|---|---|---|
| 2,597,497 A | 5/1952 | Joris | |
| 2,663,743 A | 12/1953 | Bewley et al. | |
| 2,679,535 A | 5/1954 | Lavender, Jr. et al. | |
| 2,737,480 A | 3/1956 | Adams et al. | |
| 2,744,144 A | 5/1956 | Sheffield | |
| 3,671,422 A | 6/1972 | Morrow | |
| 3,963,610 A * | 6/1976 | Hauschulz | 210/21 |
| 3,996,111 A | 12/1976 | Hanotier | |
| 4,001,341 A | 1/1977 | Welch et al. | |
| 4,158,611 A | 6/1979 | Cooke | |
| 4,262,151 A | 4/1981 | Pujado | |
| 4,385,982 A | 5/1983 | Anderson | |
| 4,447,655 A | 5/1984 | Mendiratta | |
| 4,469,561 A | 9/1984 | Sikdar et al. | |
| 4,504,364 A | 3/1985 | Chen et al. | |
| 4,652,375 A | 3/1987 | Heilweil et al. | |
| 5,338,453 A * | 8/1994 | Fraini | 210/634 |
| 5,510,543 A | 4/1996 | Fulmer et al. | |
| 5,656,152 A | 8/1997 | McLaughlin et al. | |
| 5,948,242 A | 9/1999 | Ohsol et al. | |
| 5,962,751 A * | 10/1999 | Dyckman | 568/757 |
| 6,034,282 A | 3/2000 | Dyckman et al. | |
| 2001/0000260 A1 * | 4/2001 | Taggart | 568/715 |

FOREIGN PATENT DOCUMENTS

| | | |
|---|---|---|
| DE | 1 543 497 | 9/1969 |
| DE | 91643 | 8/1972 |
| DE | 25 22 512 | 12/1975 |
| DE | 25 41 489 | 4/1976 |
| EP | 0 032 255 | 7/1981 |
| EP | 0 064 447 | 11/1982 |
| EP | 0 134 088 | 3/1985 |
| EP | 0 713 850 | 5/1996 |
| GB | 756405 | 9/1956 |
| GB | 849987 | 9/1960 |
| WO | WO-00/66523 A | * 11/2000 |

OTHER PUBLICATIONS

Patent Abstracts of Japan, JP 56–065835, Jun. 3, 1981.
Chemical Abstracts, EP 265 598, May 4, 1988 109:25171 p.
Chemical Abstracts, DE 207 309, Feb. 22, 1984 101:97457u.
Abstracts, JP 57–025385, Feb. 10, 1982.
Abstracts, SU 673 612, Jul. 19, 1979.
Abstracts, SU 1544 761, Feb. 23, 1990.
Patent Abstracts of Japan, JP 47–032507, Aug. 19, 1972.
Abstracts, D. Bartley, "Heavy crudes, stocks pose desalting problems" 1985, oil Gas J., vol. 80 p. 117–124.
Robert H. Perry, et al., Chemical Engineers' Handbook, Fifth edition, "Phase equilibriums" p. 15–14 (1973).
Douglas M. Considine, Chemical and Process Technology Encyclopedia, "Petroleum processing" p. 856 (1974).
Zakoshansky et al. *Petrochemical & Refinery Issue No. 6* (Moscow (1988)).

* cited by examiner

*Primary Examiner*—Michael L. Shippen
(74) *Attorney, Agent, or Firm*—Oblon, Spivak, McClelland, Maier & Neustadt, P.C.

(57) ABSTRACT

A process for reducing the salt content of fractions comprising high boilers obtained in the preparation of phenol from cumene, by extraction, is claimed. In the preparation of phenol from cumene, not only phenol and acetone but also by-products such as dimethyl phenyl carbinol or acetophenone are formed in the cleavage of cumene hydroperoxide. In the work-up of the cleavage product phase by distillation, these by-products are obtained as a fraction which boils only at high temperatures. These fractions further comprise alkali metal in the form of salts as a result of the neutralization by means of aqueous sodium hydroxide after the acid catalyzed cleavage. The presence of salt in this phase makes the work-up of this phase considerably more difficult. The salt is usually removed from the fraction by extraction of the fraction with water. However, considerable problems can occur if the aqueous phase cannot be cleanly separated from the organic phase. According to the invention, not only water but also an organic liquid is added to the fractions comprising high boilers for the purposes of extraction. This aids and accelerates the subsequent phase separation. The organic liquid to be added to the fractions comprising high boilers can be removed again from the treated fractions by simple distillation. Furthermore, the process of the invention lowers the phenol content of the fractions comprising high boilers and phenol is recovered.

Fractions comprising high boilers which have been treated according to the invention can be used as starting material for the production of carbon black.

15 Claims, 1 Drawing Sheet

PROCESS FOR REDUCING THE SALT CONTENT OF FRACTIONS COMPRISING HIGH BOILERS OBTAINED IN THE PREPARATION OF PHENOL FROM CUMENE, BY EXTRACTION

BACKGROUND OF THE INVENTION

1. Field of the Invention

The invention relates to a process for reducing the salt content of fractions comprising high boilers obtained in the preparation of phenol from cumene, by extraction. The process is particularly suitable for reducing the salt content of fractions comprising high boilers which already have a low phenol content, where the phenol content of the fractions comprising high boilers is further reduced by the process claimed and phenol is thereby recovered.

The invention likewise relates to the use of fractions comprising high boilers which have been extracted according to the invention as starting materials for the production of carbon black.

2. Discussion of the Background

In the preparation of phenol from cumene by the Hock process, cumene is oxidized to cumene hydroperoxide (CHP) in a first reaction step, known as oxidation. As is known, dimethyl phenyl carbinol (DMPC) and acetophenone (ACP) are formed as by-products in this step. In a second reaction step, known as cleavage, the CHP is cleaved into phenol and acetone by action of an acid, usually sulfuric acid. The product from the cleavage is subsequently neutralized with an alkali, usually aqueous sodium hydroxide, and worked up by distillation. Particularly in the cleavage, high-boiling components such as cumylphenols and indanes are formed from DMPC and these together with ACP are obtained as a high-boiling fraction (bottom product) in the distillation. Further constituents of this bottom product are alkali metal salts which get into the distillation as a result of the neutralization, and also phenol. U.S. Pat. No. 5,284,735 mentions typical a phenol content of 5-40% by weight, a ACP content of 5-30% by weight, a cumylphenol content of 10-50% by weight and a salt content of 0-2% by weight.

The bottom product or the fraction comprising high boilers is customarily incinerated as described in U.S. Pat. No. 5,283,376, by which means steam can be generated. As a further possible way of utilizing this fraction, Poll Nafta (Katowice, Poll) (1975), 31(12), 484/7, has described mixing it into asphalts, but this is problematical in the case of high phenol contents in the fractions comprising high boilers.

In the incineration of the fractions comprising high boilers, the sodium salts cause problems since they result in corrosion and emissions. The removal of these salts from the bottom product of phenol plants has been described many times. DE-B 1 219 035 describes, for example, the extraction of the salts using 10% strength sulfiric acid. U.S. Pat. No. 5,283,376 describes a process in which a fraction comprising high boilers is treated with an aqueous amine solution with the aim of simultaneously lowering the phenol content and the alkali metal content. Finally, U.S. Pat. No. 5,847,235 describes a process in which the fraction comprising high boilers is treated with water without further additives at from 10 to 90° C. in a multistage countercurrent extraction plant. Thus, according to U.S. Pat. No. 5,847,235, the salt content can be reduced from 0.139% to less than 0.001% (10 wppm) in a six-stage extraction column at 85° C. when the ratio of fraction comprising high boilers to water is 1:0.5 and the phenol content of this fraction is 17.2%. The fraction comprising high boilers forms the heavy phase in this extraction.

The phase separation between bottom product and water or aqueous solutions is, however, often incomplete. Causes are, depending on the composition of the fraction comprising high boilers or the bottom product, an insufficiently large density difference between the two phases, an excessively high viscosity of the bottom product and inhibition of coalescence at the phase interface presumably caused by the interfacial tensions being too low. Such unsatisfactory phase separations occur especially when the phenol content in the bottom product is low, i.e. below 5% by weight. Under unfavorable circumstances, the density ratios can be reversed in the extraction apparatus, i.e. contrary to the description in U.S. Pat. No. 5,847,235, the bottom product can become the lighter phase, so that malfunctions occur in the operation of such plants. Low phenol contents of less than 5% by weight in the fraction comprising high boilers and thus correspondingly low phenol losses over the entire phenol process are, however, desirable, since this increases the overall yield of the process and thus improves the economics. Such low phenol contents can be achieved by appropriate measures in the distillation, e.g. in combination with a thermal after-treatment (cracking) of the bottom products from the phenol columns as described in DE-B 1 121 621.

It is therefore an object of the present invention to provide a process for removing the salts from fractions comprising high boilers, in which optimum extraction conditions are achieved by means of good phase separations even when the fractions comprising high boilers have low phenol contents.

SUMMARY OF THE INVENTION

It has surprisingly been found that a process for reducing the salt content of fractions comprising high boilers obtained in the preparation of phenol from cumene, by extraction, in which not only an aqueous phase but also an organic phase or liquid are mixed into the streams comprising high boilers considerably simplifies the extraction and subsequent phase separation even in the case of low phenol contents in the streams comprising high boilers and also enables part of the phenol to be recovered from the fraction comprising high boilers.

The present invention accordingly provides a process for reducing the salt content of fractions comprising high boilers which are obtained in the preparation of phenol from cumene, by extraction, wherein at least one organic liquid is mixed as diluent into a fraction comprising high boilers which is to be extracted.

The present invention likewise provides for the use of a fraction comprising high boilers which has been extracted by a process as described above, as starting material for the production of carbon black.

In addition, the present invention provides for the use of a process as described above for recovering phenol from fractions comprising high boilers and containing up to 5% by weight of phenol.

The process of the invention has the advantage that mixing at least one organic phase or liquid into the fractions comprising high boilers before or during extraction with water or an aqueous phase or solution considerably simplifies the subsequent phase separation. Use of the process of the invention makes only one extraction stage and one phase separation sufficient for achieving the necessary salt content.

A further advantage of the process of the invention is that, even in the case of low phenol contents in the fractions comprising high boilers, part of the phenol can be recovered from these fractions.

In addition, mixing in an organic liquid of suitable density also makes it possible to influence the phase separation so that, for example, the organic phase is always the lighter phase (less dense) and the aqueous phase is always the heavier phase (more dense), even if the fractions comprising high boilers have a similar or even higher density compared to the aqueous phase. The advantage provided by the process of the invention in this respect is that phase separation is always ensured in the case of a continuous or batchwise process and that the organic phase is always the lighter phase so that it is not possible, for example, for the organic phase instead of the aqueous phase to be passed to a water treatment plant for treatment and cause damage there.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
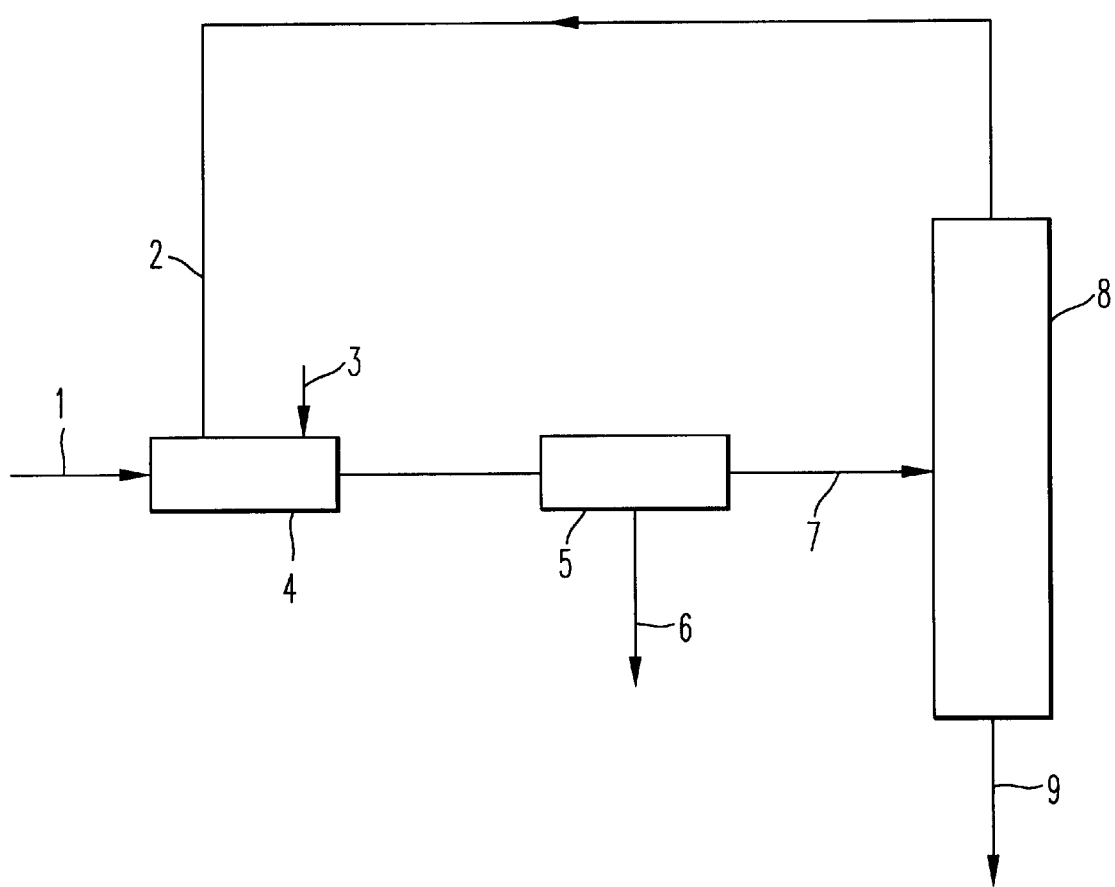
FIG. 1 schematically shows an embodiment of the process of the invention, without restricting the process to this embodiment.

For the purposes of the present invention, fractions can be streams, phases or fractions obtained in separation processes, e.g. distillations, flash evaporations or phase separations. A fraction in the context of the present invention can be comprised of a plurality of combined fractions which, for example, are obtained in various distillation columns in phenol production.

In the following, the process of the invention will be described by way of example for the work-up of streams obtained in the preparation of phenol from cumene, without being restricted thereto.

In the preparation of phenol from cumene by the Hock process, cumene is oxidized to cumene hydroperoxide (CHP) in a first step. This CHP is cleaved in a further step. Cleavage is preferably carried out in the presence of an acid catalyst, particularly preferably sulfuric acid. The resulting cleavage product phase, which may comprise phenol, acetone, unreacted cumene and also by-products such as acetophenone (ACP), dimethyl phenyl carbinol (DMPC), cumyl phenols and indanes, is usually neutralized and then worked up by distillation. The work-up by distillation results in fractions comprising high boilers in which alkali metal salts or alkaline earth metal salts formed in the neutralization are present as bottom products to reduce the salt content of these fractions comprising high boilers by extraction according to the invention, at least one organic phase or liquid is mixed as diluent into these fractions. The fractions comprising high boilers can be treated individually or can be combined to form one fraction prior to the treatment according to the invention. As extractant, an aqueous phase or solution is mixed into this mixture of fraction comprising high boilers and diluent. This mixture is intensively mixed to extract the salts from the organic mixture.

As organic phase or liquid, it is possible to use all organic liquids or phases which are completely miscible with the streams comprising high boilers, for example, it is possible to use hydrocarbons such as cumene as diluents. The diluents used preferably is comprised of only of organic compounds which undergo no chemical reactions with the compounds present in the streams comprising high boilers. Preference is given to using organic phases or liquids which can also be separated again from the fractions comprising high boilers simply and cleanly, preferably by distillation. Depending on the desired density of the organic mixture of fractions or fraction comprising high boilers and organic liquid, use is made of an organic liquid or phase which has a lower, equal or only slightly higher density than the fractions comprising high boilers. Very particularly preferably the organic liquid or phase mixed into the fractions comprising high boilers is cumene, since it is available in the Hock process.

As aqueous phase, preference is given to using water. It can be advantageous for the water used to contain a low concentration of mineral acids or organic acids, preferably sulfuric acid. Very particular preference is given to using water containing from 0 to 5% by weight of an acid, particularly preferably from 2 to 4% by weight of an acid, preferably sulfuric acid, as aqueous phase. The fraction comprising high boilers which is to be extracted is preferably mixed with such an amount of diluent that the mass ratio of diluent to fraction comprising high boilers to be extracted is from 0.2:1 to 1:1, preferably from 0.4:1 to 0.6:1. Preferably, sufficient aqueous phase or solution is mixed into this mixture for the mass ratio of aqueous phase, i.e. the extractant, to fraction comprising high boilers to be from 0.1:1 to 1:1, particularly preferably from 0.2:1 to 0.5:1.

The mixing of the organic phase or liquid with the aqueous phase and the fraction comprising high boilers can be carried out using any apparatus suitable for generating liquid/liquid dispersions, for example by means of a static mixer, stirred apparatuses or simply by means of a centrifugal pump.

The mixture of organic phase or liquid, aqueous phase and streams comprising high boilers is transferred to a suitable separation apparatus. In this separation apparatus, the aqueous phase, in which the salts present in the organic phase have accumulated as a result of the mixing with the organic phase comprised of diluent and fraction comprising high boilers, is separated from the organic phase. As separation apparatus, it is possible to use any separation apparatus suitable for the separation of liquid/liquid mixtures. The separation apparatus used is preferably a gravity separator, with or without internals, or a centrifuge, most preferably a plate separator.

The extraction, i.e. the mixing of the phases and the subsequent phase separation, is preferably carried out at a temperature of from 20 to 90° C. The extraction and subsequent phase separation are particularly preferably carried out at a temperature of from 40 to 70° C.

The fractionation of the organic phase separated from the aqueous phase in the separation apparatus, which follows the phase separation and serves to recover the organic liquid added as diluent from the phase comprising high boilers, is preferably carried out by thermal means. This thermal separation can, for example, be carried out in a distillation column or a falling film evaporator. The way in which the thermal separation of the diluent is carried out depends on the desired or permissible residual diluent content which is permitted or desired in the fraction comprising high boilers which has been extracted. When using cumene as diluent, residual cumene contents of less than 1% in the fraction comprising high boilers after extraction is appropriate, so that the overall yield of the phenol process is not unnecessarily impaired.

It may be advantageous to reuse all or at least some of the diluent recovered in the thermal separation for diluting fractions comprising high boilers which have yet to be worked up.

The process of the invention can be carried out continuously or batchwise. It can be advantageous to carry out substeps of the process of the invention one or more times. Thus, for example, it can be useful to carry out the thermal separation of the diluent in one or more distillation columns in order to remove the diluent as completely as possible from the fraction comprising high boilers which has been extracted.

Likewise, it can be advantageous to carry out not only one extraction step but a plurality of extraction steps. In this embodiment of the process of the invention, the mixture of diluent and fraction comprising high boilers is mixed with an aqueous phase as extractant. After the aqueous phase has been separated off, the remaining organic mixture is again intensively mixed with an aqueous phase. This procedure can be repeated until the desired salt content of the fraction comprising high boilers which has been extracted is reached.

It has been found that even a single extraction step according to the present invention reduces the salt content of a fraction comprising high boilers from an initial sodium content of 1500 wppm of sodium to a sodium content of less than 100 wppm, preferably less than 50 wppm, which is sufficient for the purposes of incineration.

In addition, it has surprisingly been found that a fraction comprising high boilers which has been worked up by this process to a sodium content of less than 20 wppm can be used for carbon black production, or at least can be mixed in proportions of up to 50%, preferably at least in proportions of up to 20%, into the known raw materials for carbon black production, for example coal tar oils or petrochemical oils from naphtha production. Compared to simple incineration, the use of a fraction comprising high boilers which has been extracted according to the invention as starting material for the production of carbon black represents a significant increase in value.

Furthermore, it has surprisingly been found that not only salts but also part of the phenol present in the fraction comprising high boilers is extracted by the aqueous phase and can be recovered via subsequent work-up of the aqueous phase. The work-up of the aqueous phase for the recovery of the phenol can be carried out in a manner known to those skilled in the art, e.g. by extraction of the aqueous phase with cumene and subsequent work-up of the cumene phase by distillation.

The process of the invention can be used for recovering phenol from fractions comprising high boilers and up to 5% by weight of phenol. Preferably up to 25%, very particularly preferably up to 50%, of the phenol present in a fraction comprising high boilers is recovered by the extraction according to the invention.

FIG. 1 schematically shows an embodiment of the process of the invention, without restricting the process to this embodiment.

The fraction 1 comprising high boilers is intensively mixed with an organic liquid 2 used for dilution and an aqueous solution 3 serving as extractant by means of a mixing apparatus 4. In a subsequent separation apparatus 5, the now salt- and phenol-containing aqueous phase 6 is taken off. In a thermal separation apparatus 8, the diluent 2 is finally separated off again from the organic phase 7 and recirculated. A now salt-free fraction 9 comprising high boilers is obtained as product.

As mixing apparatus 4, it is possible to use any apparatus suitable for generating liquid/liquid dispersions, e.g. static mixers, stirred apparatuses or simply a centrifugal pump. As separation apparatus 5, it is possible to use a simple gravity separator with or without internals or else a centrifuge. As apparatus 8 for the thermal separation of the diluent, it is possible to use, for example, a distillation column or a falling film evaporator.

The process of the invention is illustrated by the following examples, without it being restricted to these.

EXAMPLE 1
(Comparative Example)

A fraction comprising high boilers, which contained about 3.5% by weight of phenol and 0.14% by weight of Na, was mixed at about 90° C. with water in a ratio of fraction comprising high boilers:water=3:1. After mixing, an attempt was made to separate the organic phase from the aqueous phase. Even after a number of hours, complete phase separation had not occurred. Due to residues of dispersed aqueous solution in the fraction comprising high boilers, the Na contents in multiple tests fluctuated in the range from 0.01 to 0.05% by weight.

EXAMPLE 2
(According to the Invention)

A fraction comprising high boilers as described in Example 1 was mixed at 30° C. with cumene and 5% strength sulfuric acid in a ratio of fraction: cumene : sulfuric acid of 2:1:1. After mixing, phase separation occurred. After separation of the two liquid phases and removal of the cumene by distillation, the Na content of the fraction comprising high boilers was 0.0045% (45 wppm).

EXAMPLE 3
(According to the Invention)

A fraction comprising high boilers as described in Example 1 was mixed at 90° C. with cumene and 5% strength sulfuric acid in a ratio of fraction:cumene:sulfuric acid of 1:1:0.5. After separation of the two liquid phases and removal of the cumene by distillation, the Na content of the fraction comprising high boilers was less than 0.0005% (5 wppm). The phenol content of the fraction comprising high boilers was reduced by the extraction process from an initial 3.9% by weight to 2.9% by weight. A fraction comprising high boilers which had been worked up in this way could be mixed into a raw material for carbon black production in a ratio of 1:4.

Obviously, numerous modifications and variations of the present invention are possible in light of the above teachings. It is therefore to be understood that within the scope of the appended claims, the invention may be practiced otherwise than as specifically described herein.

This application is based on German patent application 19954141.8-44 filed in the German Patent Office on Nov. 11, 1999, the entire contents of which are hereby incorporated by reference

What is claimed is:

1. A process for reducing the salt content of fractions comprising high boilers obtained in the preparation of phenol from cumene comprising:

i) diluting a fraction comprising high boilers containing up to 5% by weight of phenol with a diluent comprising at least one organic liquid; and ii) extracting said diluted fraction comprising high boilers with an acidic aqueous phase containing up to 5% by weight of an acid.

2. The process as claimed in claim 1 wherein said extracting comprising mixing intensively, an aqueous phase into a mixture of said diluent and said fraction comprising high boilers, and, further comprising separating said aqueous phase by liquid/liquid separation.

3. The process as claimed in claim 1 further comprising separating said diluent from said fraction comprising high boilers after said extraction by thermal separation.

4. The process as claimed in claim 1 wherein a ratio of said diluent to said fraction comprising high boilers is from 0.2:1 to 1:1 w/w.

5. The process as claimed in claim 1 wherein said diluent comprises cumene.

6. The process as claimed in claim 2 wherein a ratio of said aqueous phase to said the fraction comprising high boilers is from 0.1:1 to 1:1 w/w.

7. The process as claimed in claim 1, wherein said aqueous phase contains from 3to 4% by weight of sulfuric acid.

8. The process as claimed in claim 2 wherein said intensive mixing and said liquid/liquid separation are each independently carried out at a temperature of from 20 to 90° C.

9. The process as claimed in claim 8 wherein said temperature is 40 to 70° C.

10. The process as claimed in claim 3 wherein said mixing is carried out in a static mixer and said phase separation is carried out in a centrifuge.

11. The process as claimed in claim 10 wherein said centrifuge is a plate separator.

12. The process as claimed in claim 1, wherein said fraction comprising high boilers comprises phenol and at least a part of said phenol is recovered by means of the extraction.

13. The process as claimed in claim 12 wherein up to 50% of the phenol present in said fraction comprising high boilers is recovered by means of said extraction.

14. A method of producing carbon black comprising:
i) preparing phenol from cumene, producing a fraction comprising high boilers,
ii) diluting said fraction comprising high boilers contains up to 5% by weight of phenol with a diluent comprising at least one organic liquid;
iii) extracting said diluted fraction comprising high boilers with an acidic aqueous phase containing up to 5% by weight of an acid,
wherein said fraction comprising high boilers contains up to 5% by weight of phenol; and
iv) combusting an extracted fraction comprising high boilers.

15. A method of recovering phenol from fractions comprising high boilers comprising:
i) preparing phenol from cumene, producing a fraction comprising high boilers which comprises up to 5 wt. % of phenol,
ii) diluting said fraction comprising high boilers which comprises up to 5 wt. % of phenol with a diluent comprising at least one organic liquid;
iii) extracting said diluted fraction comprising high boilers which comprises up to 5 wt. % of phenol with an acidic aqueous phase containing up to 5% by weight of an acid,
wherein said fraction comprising high boilers contains up to 5% by weight of phenol,
iv) recovering phenol from an extracted fraction comprising high boilers which comprises up to 5 wt. % of phenol.

* * * * *

UNITED STATES PATENT AND TRADEMARK OFFICE
CERTIFICATE OF CORRECTION

PATENT NO. : 6,489,518 B1
DATED : December 3, 2002
INVENTOR(S) : Manfred Weber et al.

It is certified that error appears in the above-identified patent and that said Letters Patent is hereby corrected as shown below:

Column 7,
Lines 2 and 4, "comprising", should read -- comprises --.
Line 15, "said the", should read -- the said --.
Line 18, "3to", should read -- 3 to --.
Line 26, "Claim 3", should read -- Claim 2 --.

Column 8,
Line 5, "contains", should read -- containing --.

Signed and Sealed this

Nineteenth Day of August, 2003

JAMES E. ROGAN
*Director of the United States Patent and Trademark Office*